US00PP34557P2

(12) United States Plant Patent
Shoup

(10) Patent No.: US PP34,557 P2
(45) Date of Patent: Sep. 13, 2022

(54) CLIMBING ROSE NAMED 'HEAVENLY ASCENT'

(50) Latin Name: *Rosa hybrida*
Varietal Denomination: Heavenly Ascent

(71) Applicant: George Michael Shoup, Brenham, TX (US)

(72) Inventor: George Michael Shoup, Brenham, TX (US)

( * ) Notice: Subject to any disclaimer, the term of this patent is extended or adjusted under 35 U.S.C. 154(b) by 0 days.

(21) Appl. No.: 17/372,159

(22) Filed: Jul. 9, 2021

(51) Int. Cl.
*A01H 5/02* (2018.01)
*A01H 6/74* (2018.01)

(52) U.S. Cl.
USPC ..... Plt./111

(58) Field of Classification Search
USPC ..... Plt./101, 109, 111
See application file for complete search history.

*Primary Examiner* — Karen M Redden

(57) ABSTRACT

A new and distinct variety of climbing rose plant, herein referred to by its cultivar name, 'Heavenly Ascent', is provided which abundantly and continuously forms extremely fragrant blooms. The growth habit is climbing. The foliage is dark green, leathery, and semi-glossy. The plant propagates from cuttings easily, blooms profusely throughout the season, especially for a climbing rose, and is notable for possessing both fragrance and disease resistance. The new variety is well suited to growing as attractive ornamentation and a source of fragrance in in the landscape.

1 Drawing Sheet

Botanical/commercial classification: Latin name—*Rosa hybrida.*

Varietal denomination: 'Heavenly Ascent'.

SUMMARY OF THE INVENTION

The new variety of *Rosa hybrida* climbing rose plant was created at Brenham, Tex., U.S.A., by artificial pollination wherein two parents were crossed which previously had been observed in the hope that each would contribute their desired traits. The female parent (i.e., the seed parent) was the 'Doreen's Centennial' variety (non-patented). The male parent (i.e., the pollen parent) was the 'KORberonem' variety (U.S. Plant Pat. No. 26,747). The parentage of the new variety can be summarized as follows:

'Doreen's Centennial' x 'KORberonem'

The seeds resulting from the above pollination were stratified in an artificial environment and sown into trays in a greenhouse environment. Seedlings were obtained and displayed phenotypic and biological variation. Selective trialing and evaluation of the seedlings resulted in the identification of a single plant of the new variety.

It was found that the new climbing rose plant of the present invention possesses the following combination of characteristics:

(a) abundantly and continuously forms blooms throughout the season,
(b) exhibits a climbing growth habit,
(c) forms blooms containing a strong fragrance,
(d) forms disease resistant foliage with a leathery and semi-glossy finish,
(e) is well suited for growing as attractive ornamentation and a source of fragrance in in the landscape.

The new rose can be distinguished from its ancestors by inspecting the blossoms. More specifically, the new rose has more bloom power and total bloom coverage when blossoming than the male pollen parent 'KORberonem'. In addition, the new rose also has a consistently stronger detectable fragrance than the seed parent, 'Doreen's Centennial'. The new rose can also be readily distinguished from its ancestors upon observing the growth rate. More specifically the new rose has an approximately 20% faster growth rate than both of its parental varieties.

The new variety of the present invention also can be readily distinguished from other climbing rose plants, including the 'The New Dawn' variety (U.S. Plant Pat. No. 1) upon observation of the disease resistance of the foliage. For example, the 'The New Dawn' variety forms foliage susceptible to black spot *Diplocarpon rosae*, which is dissimilar to the foliage of 'Heavenly Ascent' which exhibits resistance to black spot *Diplocarpon rosae.*

Asexual reproduction of 'Heavenly Ascent' was done by taking cuttings in Brenham Tex., U.S.A. in beginning in 2019. Cuttings were taken from mature stems that were approximately 10 to 15 cm in length and approximately 0.75 cm in diameter. Initial cuttings were taken of the new variety and grew into mature plants. Subsequent cuttings were taken of the initial asexually reproduced plants and grown into mature plants. Mature plants of both the initially propagated plants and the subsequently propagated plants were compared. There was no observable difference between the generations. Therefore, it was demonstrated that the characteristics of 'Heavenly Ascent' remain stable, uniform and true to type in successive generations of asexual reproduction.

BRIEF DESCRIPTION OF THE DRAWING

The accompanying color illustration shows as true is as is reasonably possible to obtain in color photographs of this type, the typical characteristics of the plant parts, i.e., the flowers, buds, stems and leaves of the new rose, 'Heavenly Ascent'. The illustrated rose plant parts were approximately one year of age and were observed during August, while growing on their own roots in Brenham, Tex., U.S.A. Flowers, buds, and stem growth are displayed in various stages of maturity. The upper side and under side of the leaves, blooms and petals are displayed.

DETAILED BOTANICAL DESCRIPTION

The chart used in the identification of colors is The Royal Horticultural Society Colour Chart (R.H.S. Colour Chart) Edition V. The description is based on fully mature specimens of the new variety.

Class: Climbing rose named, 'Heavenly Ascent'.

Plant:

*Height*.—Approximately 2.1 to 3 meters on average at maturity.

*Width*.—Approximately 1.2 to 1.5 meters on average at maturity.

*Habit*.—Assurgent and ascending.

Stems:

*Size*.—Approximately 137 cm tall by 1.2 cm in caliper.

*Color*.—Young stems: Greyed-Red Group 178C. Adult wood: Yellow-Green Group 146B.

*Prickles*.—Size: Approximately 0.8 cm in length on average. Quantity: Average. Color: Greyed-Orange Group 177A. Shape: Declining. Density: Average density and evenly spaced throughout the stems.

*Texture*.—Smooth.

*Internodal spacing*.—Approximately 11 cm on average.

Leaves:

*Arrangement*.—Alternate, odd-pinnate, and compound.

*Margin*.—Serrate.

*Stipules*.—Size: Approximately 19 mm×7 mm on average. Margin: Adnate with winged tips. Color: Green Group 135A. Texture: Smooth.

*Size*.—Approximately 17 cm×11.5 cm on average.

*Petioles*.—Upper surface: Yellow-Green Group 146B. Under surface: Green Group 143C to 143D. Size: Approximately 8.5 cm×1 mm on average. Shape: Filiform.

*Rachis*.—Color: Green Group 143C to 143D.

*Leaflets*.—Number: 5 and 7. Shape: Ovate, with an acute apex and cordate base. Texture: Smooth. Size: Approximately 5.5 cm×4 cm on average. Venation: Reticulate. Venation Color: Yellow-Green Group 146B. Apex: Acute. Base: Obtuse. Overall appearance: Dark-green, leathery and semi-glossy. Texture Upper Surface: Slightly waxy. Texture Under Surface: Matte. Color (young foliage) upper surface: Greyed-Purple Group 185A. Color (young foliage) under surface: Greyed-Purple Group 185B. Color (adult foliage) upper surface: Green Group 135A to 135B. Color (adult foliage) under surface: Yellow-Green Group 147B.

Inflorescence:

*Average size of inflorescence*.—Approximately 17 cm×14 cm on average.

*Number of flowers per inflorescence*.—Approximately 5 to 7 on average.

*Peduncle*.—Color: Yellow-Green Group 144B. Length: Approximately 6.5 cm on average. Diameter: Approximately 2.5 mm on average. Texture: Slightly gland-ciliate.

*Sepals*.—Number: 5. Size: Approximately 2 cm×0.8 cm on average. Arrangement: Pentamerous and imbricate. Shape: Obcunate. Margin: Gland-ciliate. Apex: Leaf-pointed. Base: Truncate. Texture: Slightly pubescent. Upper surface: Green Group 143B to 143C. Under surface: Green Group 143A to 143C.

*Buds*.—Shape: Pointed ovoid (as illustrated). Length: Approximately 2.2 cm to 3 cm on average. Size: Medium. Color (when opening) upper surface: Yellow Group 14D. Color (when opening) under surface: Yellow Group 13D.

Flower:

*Form*.—Rosette to occasional button.

*Diameter*.—Approximately 8 cm on average.

*Color*.—(when opening) upper surface: Yellow Group 11D. (when opening) under surface: Yellow Group 11C. (when blooming) upper surface: Yellow-White Group 158B. (when blooming) under surface: Yellow-White Group 158B. (end of blooming) upper surface: Yellow-White Group 158C. (end of blooming) under surface: Yellow-White Group 158C.

*Fragrance*.—Tart and sweet with a blend of apple, musk, vanilla, and cherry.

*Petals*.—Petal Size: Approximately 3 cm×2.5 cm on average. Petal Form: Obovate. Petal Number: Approximately 75 on average. Petaloids: None present. Petal Drop: Easily and cleanly after blooming. Apex: Very slightly mucronate. Base: Cunate. Margin: Entire. Texture: Glabrous.

*Lasting quality*.—On plant: Approximately 5-7 days on average. In vase: Unknown.

*Petal drop*.—Easily and cleanly after blooming.

*Stamen number*.—Approximately 40 to 45 on average.

*Anther color*.—Yellow-Orange Group 20A.

*Anther shape*.—Oblong.

*Anther length*.—Approximately 2 mm on average.

*Filament color*.—Yellow Group 3B.

*Filament length*.—Approximately 6 mm on average.

*Pollen quantity*.—Average amount of pollen produced.

*Pollen color*.—Yellow-Orange Group 17B.

*Pistil form*.—Separate and free.

*Pistil number*.—Approximately 45 on average.

*Stigma color*.—Yellow-Orange Group 22B.

*Style color*.—Red Group 50B.

*Style length*.—Approximately 0.6 cm on average.

*Receptacle*.—Achenes form on the inside of the fruit. Size: Approximately 2 cm×2 cm on average when mature.

*Rate of flower opening*.—Average.

*Lasting quality*.—On plant: Approximately 3 to 4 days on average. In vase: Unknown.

Development:

*Vegetation*.—Above average vigor.

*Growth rate*.—Fast.

*Hip/seed formation*.—Average. Occasionally formed from open pollination.

Root system:

*Root color*.—Yellow-White Group 158C.

*Root habit*.—Well rounded.

Physiology:

*Disease resistance*.—Resistant to all tested races of black spot *Diplocarpon rosae*, and above average resistance to powdery mildew *Podosphaera pannosa*. Susceptible to downy mildew *Peronospora sparsa*.

*Cold hardiness*.—The variety has been found to be suitable for climactic conditions in USDA Plant Hardiness Zone 8. Based on the performance of the parental varieties, it is likely, although untested, that the new variety is also suitable for climatic conditions of USDA Plant Hardiness Zones 5, 6 and 7.

*Heat tolerance*.—The variety exhibits average heat tolerance. The variety has been found to be suitable for climactic conditions in USDA Plant Hardiness Zone 8. Based on the performance of its parent varieties, it is likely, although untested, that the new variety is also suitable for climatic conditions of USDA Plant Hardiness Zone 9.

*Drought tolerance*.—The variety exhibits average drought tolerance.

I claim:

1. A new and distinct climbing rose plant characterized by the following combination of characteristics:

1) abundantly and continuously forms blooms throughout the season,
2) exhibits a climbing growth habit,
3) forms blooms containing a strong fragrance,
4) forms disease resistant foliage with a leathery and semi-glossy finish,
5) is well suited for growing as attractive ornamentation and a source of fragrance in in the landscape, substantially as herein illustrated and described.

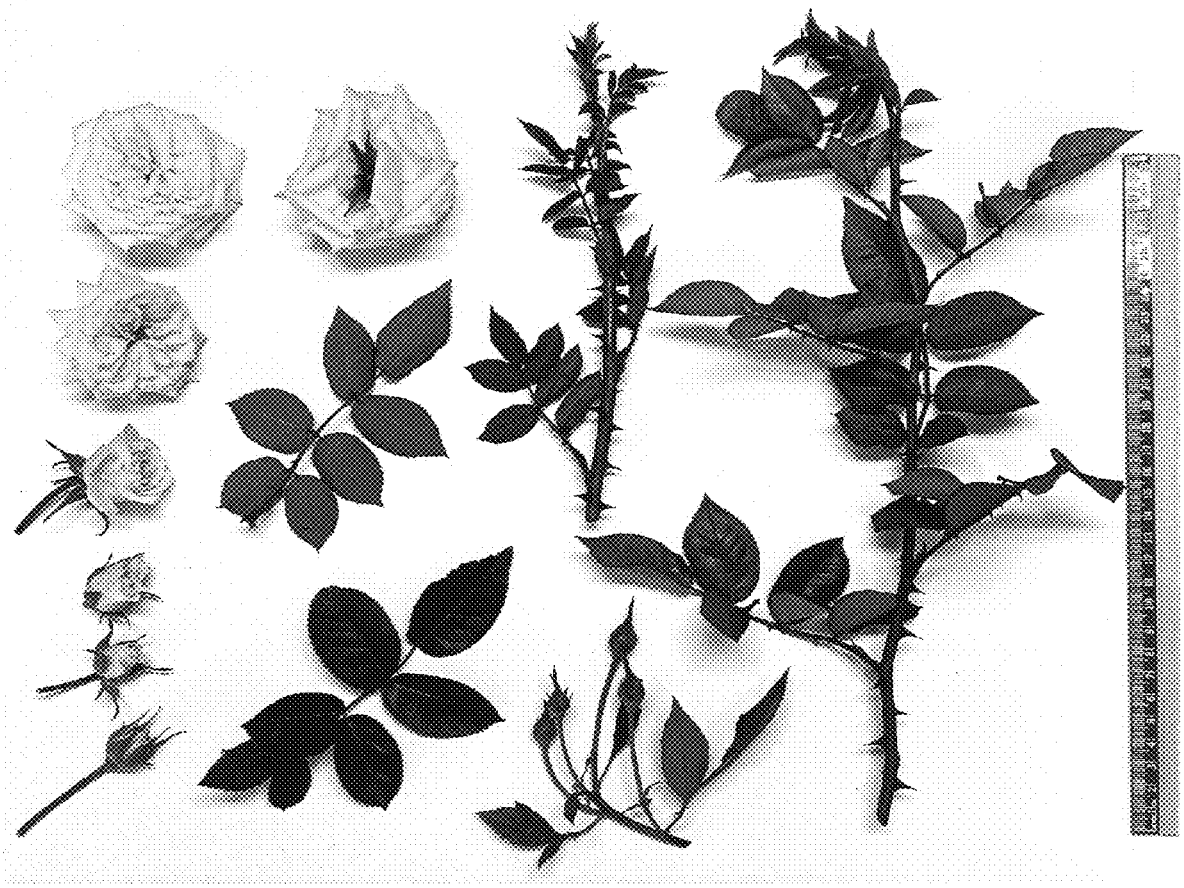

* * * * *